United States Patent
Pasquier et al.

(10) Patent No.: US 7,070,625 B2
(45) Date of Patent: Jul. 4, 2006

(54) AGENT AND METHOD FOR COLORING KERATIN FIBERS CONTAINING 2-BENZOTHIAZOLINONE-HYDRAZONE AND QUINONE DERIVATIVES

(75) Inventors: Cécile Pasquier, Marly (CH); Gisela Umbricht, Marly (CH); Veronique Buclin-Charrière, Morlon (CH); Sylviane Oberson, Ecuvillens (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 470 days.

(21) Appl. No.: 10/250,847

(22) PCT Filed: Aug. 22, 2002

(86) PCT No.: PCT/EP02/09381

§ 371 (c)(1),
(2), (4) Date: Jul. 14, 2003

(87) PCT Pub. No.: WO03/042199

PCT Pub. Date: May 22, 2003

(65) Prior Publication Data

US 2004/0060124 A1 Apr. 1, 2004

(30) Foreign Application Priority Data

Nov. 14, 2001 (DE) .......................... 101 55 907

(51) Int. Cl.
*A61K 7/13* (2006.01)

(52) U.S. Cl. .............. 8/405; 8/426; 8/437; 8/454; 8/455; 8/575; 548/146; 552/293

(58) Field of Classification Search ............. 8/405, 8/426, 437, 454, 455, 575; 548/146; 552/293
See application file for complete search history.

(56) References Cited

U.S. PATENT DOCUMENTS

| 3,869,454 A | 3/1975 | Bugaut | 260/244 |
| 5,879,411 A * | 3/1999 | Braun et al. | 8/405 |

FOREIGN PATENT DOCUMENTS

| DE | 1 049 381 | 12/1956 |
| DE | 114 415 | 8/1975 |
| DE | 43 35 624 A1 | 6/1995 |
| EP | 0 460 996 A | 12/1991 |
| EP | 0 848 942 A | 6/1998 |
| JP | 51019767 | 2/1976 |
| JP | 51019767 A * | 2/1976 |

OTHER PUBLICATIONS

English abstract of the Japanese Patent No. 51019767 A dated Feb. 1976.*
Espin J. C. et al: "Inhibition of Mushroom Polyphenol Oxidase . . . " J. Agric. Food Chem., BD. 46, NR. 8, 1998 pp. 2976–2980.

* cited by examiner

*Primary Examiner*—Eisa Elhilo
(74) *Attorney, Agent, or Firm*—Michael J. Striker

(57) ABSTRACT

The objects of the present invention are an agent (A) for coloring fibers obtained by mixing two components (A1) and (A2), characterized in that component (A1) contains at least one 2-benzothiazolinone hydrazone derivative of formula (I) or a physiologically tolerated salt thereof

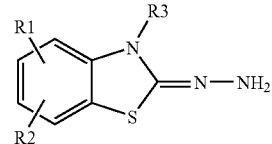

(I)

and component (A2) contains at least one ortho-quinone of formula (II) or a para-quinone of formula (III),

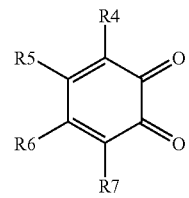

(II)

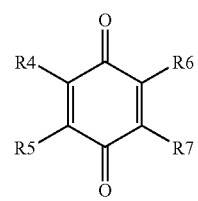

(III)

a method for coloring hair by use of said agent and a multicomponent kit for coloring hair.

10 Claims, No Drawings

AGENT AND METHOD FOR COLORING KERATIN FIBERS CONTAINING 2-BENZOTHIAZOLINONE-HYDRAZONE AND QUINONE DERIVATIVES

The objects of the present application are an agent for coloring keratin fibers, for example silk, wool or hair and particularly human hair, said agent containing a combination of (i) at least one 2-benzothiazolinone hydrazone derivative and (ii) at least one quinoid compound, and a method for coloring keratin fibers by use of said agent.

Depending on the initial color of the hair to be colored and the desired end result, hair colorants are divided mainly into oxidative colorants and toners. Oxidative hair colorants are eminently suited for covering large gray areas. Oxidative colorants used for coloring areas with up to 50% gray hair are usually referred to as oxidative toners, whereas oxidative colorants used for areas with more than 50% gray hair or colorants used for "brightening" are usually called oxidative colorants. Direct dyes are contained mainly in nonoxidative colorants (so-called toning agents). Some direct dyes, for example the nitro dyes, because of their small size, can penetrate into the hair and color it directly, at least in its outer regions. Such toners are very gentle to the hair and as a rule withstand 6 to 8 hair washings. Direct dyes are often also used in oxidative colorants to create certain shades or to intensify the color.

Moreover, coloring systems based on benzoquinones and compounds containing amino groups and/or hydroxyl groups have already been described in European laid open Patent Application EP 0 848 942, German laid open Patent Application DE 43 35 624 and European Patent EP 0 460 996.

The hitherto known colorant systems, however, cannot meet the requirements placed on colorants in all respects. For this reason, there continues to exist a considerable need for colorants which, particularly under mild conditions, produce intense and at the same time gentle colorations.

Surprisingly, we have now found that by use of a combination of (i) at least one 2-benzothiazolinone hydrazone derivative and (ii) at least one quinoid compound intense colorations in the yellow to brown color range can be produced in gentle manner under mild conditions.

An object of the present invention therefore is an agent (A) for coloring fibers, for example wool, silk, cotton or hair and particularly human hair, which agent is prepared before use by mixing two components (A1) and (A2) and is characterized in that component (A1) contains at least one 2-benzothiazolinone hydrazone derivative of formula (I) or a physiologically tolerated salt thereof

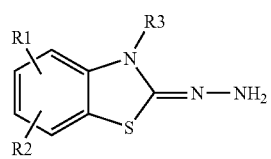

(I)

wherein

R1 and R2 can be equal or different and independently of each other denote hydrogen, a halogen atom (F, Cl, Br, I), a $(C_1-C_4)$-alkyl group, a halogen (F, Cl, Br, I)-substituted $(C_1-C_4)$-alkyl group, a $(C_1-C_4)$-alkoxy group, a sulfo group, a sulfamoyl group, a carboxyl group, a nitro group, an acetamido group or an $NR^aR^b$ group wherein the $R^a$ and $R^b$ groups can be equal or different and independently of each other denote hydrogen, a $(C_1-C_6)$-alkyl group, a carbocyclic or heterocyclic, substituted or unsubstituted aromatic grouping, or $R^a$ and $R^b$ together with the nitrogen atom form a saturated or unsaturated, substituted or unsubstituted heterocyclic $(C_3-C_6)$ group (for example an imidazolidino, piperidino, pyrrolidino, pyrazolidino, piperazino or morpholino group); or R1 and R2 together with the remainder of the molecule form a heterocyclic or carbocyclic, substituted or unsubstituted ring system;

R3 denotes a $(C_1-C_4)$-alkyl group, a halogen (F, Cl, Br, I)-substituted $(C_1-C_4)$-alkyl group, a sulfo-$(C_1-C_4)$-alkyl group, an acetyl group, a formyl group, a substituted or unsubstituted benzyl group or an isocyclic or heterocyclic grouping;

and component (A2) contains at least one ortho-quinone of formula (II) or a para-quinone of formula (III)

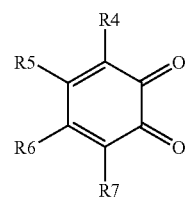

(II)

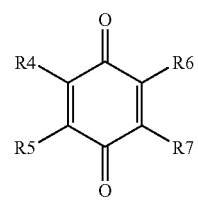

(III)

wherein

R4, R5, R6 and R7 independently of each other denote hydrogen, chlorine, bromine, fluorine, a hydroxyl group, a straight-chain or branched $(C_1-C_8)$-alkyl group, a straight-chain or branched monohydroxy-$(C_1-C_6)$-alkyl group, a straight-chain or branched polyhydroxy-$(C_2-C_6)$-alkyl group, a straight-chain or branched $(C_1-C_6)$-alkoxy group, a straight-chain or branched mono-$(C_1-C_6)$-alkoxy-$(C_1-C_6)$-alkyl group, a straight-chain or branched-poly-$(C_1-C_6)$-alkoxy-$(C_2-C_6)$-alkyl group, a $(C_1-C_2)$-alkylenedioxy group, a sulfo group, a cyano group, a straight-chain or branched amino-$(C_1-C_6)$-alkyl group, an $—NR^aR^b$ amino group wherein the $R^a$ and $R^b$ groups can be equal or different and independently of each other denote hydrogen, a $(C_1-C_6)$-alkyl group, a carbocyclic or heterocyclic, substituted or unsubstituted aromatic grouping, or $R^a$ and $R^b$ together with the nitrogen atom form a saturated or unsaturated, substituted or unsubstituted heterocyclic $(C_3-C_6)$-group (for example an imidazolidino, piperidino, pyrrolidino, pyrazolidino, piperazino or morpholino group);

or in o-quinones of formula (II) R4 and R5 and/or R6 and R7 or R5 and R6, or in p-quinones of formula (III) R4 and R5, and/or R6 and R7 always together with the remainder of the molecule form a heterocyclic or carbocyclic, substituted or unsubstituted ring.

Among the compounds of formula (I), the following 2-benzothiazolinone hydrazone derivatives are preferred:

3-methyl-2-benzothiazolinone hydrazone hydrochloride,
3-ethyl-2-benzothiazolinone hydrazone hydrochloride,
3-phenyl-2-benzothiazolinone hydrazone hydrochloride and
3-benzyl-2-benzothiazolinone hydrazone hydrochloride,
with 3-methyl-2-benzothiazolinone hydrazone hydrochloride being particularly preferred.

Some of the compounds of formula (I) are commercially available. However, they can also be prepared by methods of synthesis known from the literature, for example by methods similar to those described in German Patent DE 1 049 381, Japanese laid open Patent Application 51-019767 or East German Patent DE 114 415.

Preferred ortho-quinones of formula (II) are:

4,5-dimethoxy-3,5-cyclohexadiene-1,2-dione, 5(5H), 6(6H)-diketo-1,3-benzodioxole, 2,3-dihydro-1,4dimethyl-3-hydroxy-1H-indole-5,6-dione, 2,3-dihydro-3-hydroxy-4-methoxy-1-methyl-1H-indole-5,6-dione, 3,5-di(1,1-dimethylethyl)-3,5-cyclohexadiene-1,2-dione, 2,3-dihydro-3-hydroxy-1-methyl-1H-indole-5,6-dione, 3,4,5,6-tetrachloro-3,5-cyclohexadiene-1,2-dione, 4,5-dimethoxy-3,6-diphenyl-3,5-cyclohexadiene-1,2-dione, 4,5-di(phenylamino)-3,5-cyclohexadiene-1,2-dione, cacotheline, ammonium 3,4-dihydro-3,4-diketo-1-naphthalenesulfonate, 4-methoxy-1,2-naphthalenedione, 1,2-naphthalenedione, sodium 1,2-naphthalenedione-4-sulfonate, 4-amino-1,2-naphthalenedione hydrate (2:1) and 9,10-phenanthrene quinone. Among these, the following ortho-quinones are particularly preferred:

4,5-dimethoxy-3,5-cyclohexadiene-1,2-dione, 5(5H),6(6H)-diketo-1,3-benzodioxole, 2,3-dihydro-1,4-dimethyl-3-hydroxy-1H-indole-5,6-dione, 3,5-di(1,1-dimethylethyl)-3,5-cyclohexadiene-1,2-dione, 3,4,5,6-tetrachloro-3,5-cyclohexadiene-1,2-dione, cacotheline, 1,2-naphthalenedione, sodium 1,2-naphthalenedione-4-sulfonate, 4-amino-1,2-naphthalenedione hydrate (2:1) and 9,10-phenanthrene quinone.

Preferred para-quinones of formula (Ill) are:

1,4-benzoquinone, 2-methyl-1,4-benzoquinone, 2-tertbutyl-1,4-benzoquinone, 2-phenyl-1,4-benzoquinone, 2,5-dimethyl-1,4-benzoquinone, 2,6-dimethyl-1,4-benzoquinone, 2-methyl-5-(1-methylethyl)-1,4-benzoquinone, 2,5-ditert.butyl-1,4-benzoquinone, 2,6-ditert.butyl-1,4benzoquinone, 2,5-diphenyl-1,4-benzoquinone, 2,3,5,6-tetramethyl-1,4-benzoquinone, 2-methoxy-1,4-benzoquinone, 2-methoxy-5-methyl-1,4-benzoquinone, 2, 5-dimethoxy-1,4-benzoquinone, 2,6-dimethoxy-1,4-benzoquinone, 2,3-dimethoxy-5-methyl-1,4-benzoquinone, 2,6-dimethoxy-5-methyl-1,4-benzoquinone, 2,5-dihydroxy-1,4-benzoquinone, 2,5-dihydroxy-3-methyl-1,4-benzoquinone, 2,5-dihydroxy-3-methoxy-6-methyl-1,4-benzoquinone, 2,5-dihydroxy-3,6-diphenyl-1, 4benzoquinone, 3-hydroxy-2-methoxy-5-methyl-1,4-benzoquinone, 2-hydroxymethyl-6-methoxy-1, 4benzoquinone, 2,3,5,6-tetrahydroxy-1,4-benzoquinone, 2-bromo-1,4-benzoquinone, 2-chloro-1,4-benzoquinone, 2-fluoro-1,4-benzoquinone, 2-bromo-5-methyl-1,4-benzoquinone, 2,5-dibromo-1,4-benzoquinone, 2,5-dibromo-3,6-diphenyl-1,4-benzoquinone, 2,5-dibromo-3-methyl-6-(1-methylethyl)-1,4-benzoquinone, 2-chloro-6-methyl-1,4-benzoquinone, 2,5-dichloro-1,4-benzoquinone, 2,6-dichloro-1,4-benzoquinone, 2,5-dichloro-3,6-dimethyl-1,4-benzoquinone, 2,3-dichloro-5,6-dicyano-1,4-benzoquinone, 3,6-diketo-1,4-cyclohexadiene-1,2-dicarbonitrile, 2,5-dichloro-3,6-diketo-1,4-cyclohexadiene-1,4-dicarbonitrile, 2,5-dichloro-3,6-dihydroxy-1,4-benzoquinone, 2,5-dichloro-3,6-dimethylamino-1,4-benzoquinone, 2,3,5,6-tetrabromo-1,4-benzoquinone, 2,3,5,6-tetrachloro-1,4-benzoquinone, 2,3,5,6-tetrafluoro-1,4-benzoquinone, 2-amino-5-methyl-1,4-benzoquinone, 5-amino-2-chloro-1,4-benzoquinone, 2,5-di[(2-hydroxyethyl)amino]-1,4-benzoquinone, 2,5-diamino-3,6-dichloro-1,4-benzoquinone, 1,4-naphthalenedione, 5,8-dihydroxy-1,4-naphthalenedione and 1H-indole-4,7-dione.

Among these, the following para-quinones are particularly preferred: 1,4-benzoquinone, 2-methyl-1,4-benzoquinone, 2,5-diphenyl-1,4-benzoquinone, 2-5-dihydroxy-1,4-benzoquinone, 2,3,5,6-tetrahydroxy-1,4-benzoquinone, 2,5-[(2-hydroxyethyl)amino]-1,4-benzoquinone, 1,4-naphthalenedione, 5,8-dihydroxy-1,4-napthalenedione and 1H-indole-4,7-dione.

The compounds-of formula (I) and the ortho- or para-quinones of formulas (II) or (III) are usually stored separately from each other and are mixed only shortly before use. It is also possible, however, if the compounds of formula (I) and the ortho- or para-quinones of formulas (II) or (III) are solids, to package them together and to prepare the ready-to-use colorant (A) shortly before use by mixing the compounds of formula (I) and the ortho- or para-quinones of formula (II) or (III) with water or with a liquid preparation containing the other constituents of the colorant.

Moreover, besides the compounds of formula (I) and the ortho-quinones of formula (II) and/or the para-quinones of formula (III) in component (A2) and in the ready-to-use composition (A), the colorant according to the invention can optionally also contain other common, physiologically harmless direct dyes from the group of cationic and anionic dyes, disperse dyes, azo dyes, quinone dyes and triphenyl-methane dyes.

These direct dyes can be present in component (A2) in a total amount from about 0.02 to 20 wt. % and preferably from 0.2 to 10 wt. %, the total amount of direct dyes in the ready-to-use colorant (A) obtained by mixing components (A1) and (A2) being from about 0.01 to 10 and preferably from 0.1 to 5 wt. %.

As a rule, the colorant according to the invention consists of a mixture of components (A1) and (A2), namely a dye carrier composition (A1) containing the compound of formula (I), and another dye carrier composition (A2) containing the quinoid compound of formula (II)/(III).

Each of the compounds of formula (I) and of the ortho-quinones of formula (II) and/or para-quinones of formula (III) is contained in the dye carrier composition in question [component (A1) or component (A2)] in a total amount from about 0.02 to 20 wt. % and preferably from about 0.2 to 10 wt. %, so that the compounds of formula (I) and the ortho-quinone of formula (II) and/or para-quinone of formula (III) are each contained in the ready-to-use colorant (A) in a total amount from about 0.01 to 10 wt. % and preferably from 0.1 to 5 wt. %.

The components (A1) and (A2) as well as the ready-to-use colorant (A) can be formulated to be in the form of, for example, a solution, particularly an aqueous or aqueous-alcoholic solution, a cream, a gel or an emulsion. Their composition consists of a mixture of the compound of formula (I) or the ortho-quinones of formula (II) and/or para-quinones of formula (III) with the additives usually employed for such compositions.

Common additives to colorants used in solutions, creams, emulsions, gels or aerosol foams are, for example, solvents such as water, the lower aliphatic alcohols, for example ethanol, n-propanol and isopropanol or glycols such as glycerol and 1,2-propanediol, moreover wetting agents or emulsifiers from the classes of anionic, cationic, amphoteric or nonionic surface-active substances such as the fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty alkanolamides, ethoxylated fatty esters, furthermore thickeners such as the higher fatty alcohols, starch or cellulose derivatives, perfumes, hair pretreatment agents, conditioners, hair-swelling agents, preservatives, furthermore vaseline, paraffin oil and fatty acids as well as hair-care agents such as the cationic resins, lanolin derivatives, cholesterol, pantothenic acid and betaine. The said constituents are used in amounts usually employed for such purposes, for example the wetting agents and emulsifiers at a concentration from about 0.5 to 30 wt. % [always based on component (A1) or (A2)], the thickeners in an amount from about 0.1 to 25 wt. % [always based on component (A1) or (A2)] and the hair-care agents at a concentration from about 0.1 to 5.0 wt. % [always based on component (A1) or (A2)].

The pH of the ready-to-use colorant (A) and of the dye carrier compositions (A1) and (A2) is in each case about 3 to 12, and preferably about 4 to 10 and as a rule is reached upon mixing component (A1) with component (A2). To adjust the pH of components (A1) and (A2) and of the ready-to-use colorant (A) to the value desired for dyeing, it is possible—if necessary—to use an alkalinizing agent, for example an alkali metal hydroxide, alkaline earth metal hydroxide, alkali metal acetate (particularly sodium acetate), alkaline earth metal acetate, alkali metal carbonate (particularly sodium carbonate) or alkaline earth metal carbonate, or an acid, for example lactic acid, acetic acid, tartaric acid, phosphoric acid, hydrochloric acid, citric acid, ascorbic acid or boric acid.

The ready-to-use colorant is prepared just before use by mixing components (A1) and (A2), optionally with addition of an alkalinizing agent or an acid, and is then applied to the fibers, particularly human hair. Depending oh the depth of shade, this mixture is allowed to act for about 5 to 60 minutes and preferably for 15 to 30 minutes at a temperature of about 20 to 50° C., particularly at about 30 to 40° C. The fibers are then rinsed with water, optionally washed with a shampoo and dried.

Another object of the present invention is a multicomponent kit consisting of an agent of component (A1), an agent of component (A2) and optionally an agent for pH adjustment (alkalinizing agent or acid). Naturally, the agents of components (A1) and (A2) can consist of several individual components which are mixed with one another just before use. It is also possible to have a 2-component kit in which component 1 consists of a powder containing the compounds of formula (I) and the ortho-quinones of formula (II) and/or para-quinones of formula (III) and optionally other common powdered cosmetic additives, and whose component 2 is water or a liquid cosmetic preparation. Particularly preferred, however, is a 2-component kit consisting of an agent of component (A1) and an agent of component (A2).

The colorant of the invention imparts to the fibers, particularly keratin fibers, for example human hair, in gentle manner a uniform and lasting coloration and provides a wide range of shades from yellow to red to brown-black.

The following examples are intended to explain the subject matter in more detail without limiting its scope.

EXAMPLES

Examples 1–17

Component (A1)

4.0 g of decylpolyglucose (Plantaren ® 2000), aqueous solution
0.2 g of disodium ethylenediaminetetraacetate hydrate
5.0 g of ethanol -continued 0.59 g of 3-methyl-2-benzothiazolinone hydrazone hydrochloride hydrate
Y g of ethanol added as per Table 1
to 100.0 g demineralized water Component (A2)

X g of ortho- or para-quinone as per Table 1

The afore-indicated components were mixed uniformly with each other at room temperature (20–25° C.) or with slight heating (35–40° C.). If necessary, the pH of the ready-to-use colorant (A) was adjusted to the value shown in Table 1 with sodium hydroxide, sodium carbonate, ammonia or citric acid.

The ready-to-use hair colorant was applied to the hair and uniformly distributed with a brush. After an exposure time of 30 min at 40° C., the hair was rinsed with luke-warm water and then dried.

The amounts of the ortho- or para-quinones used and the colorations obtained are collected in the following Table 1.

The L*a*b* color values given in the examples were determined with a Chromameter II color meter supplied by Minolta. The L value indicates the brightness (i.e., the lower the L value, the higher is the color intensity), the a value being a measure of the red content (i.e., the higher the a value, the higher is the red content). The b value is a measure of the blue content of the color, i.e., the more negative the b value the higher is the blue content.

TABLE 1

| Example No. | Quinone Used | pH | Ethanol Added | Color Shade | Color Values |
|---|---|---|---|---|---|
| 1 | 4,5-Dimethoxy-1,2-benzoquinone (0.41 g) | 3.0 | 20 g | brick-red | L = 45.3<br>a = +34.8<br>b = +29.7 |
| 2 | 4,5-Dimethoxy-1,2-benzoquinone (0.41 g) | 10.1 | 20 g | fox-orange | L = 44.7<br>a = +23.5<br>b = +21.1 |
| 3 | 4,5-Methylenedioxy-o-benzoquinone (0.39 g) | 8.0 | 16 g | brown-orange | L = 53.4<br>a = +22.6<br>b = +26.9 |
| 4 | Cacotheline (1.26 g) | 7.1 | 14 g | red | L = 50.6<br>a = +32.1<br>b = +12.6 |
| 5 | 1,2-Naphthoquinone (0.38 g) | 7.1 | 20 g | orange-red | L = 50.7<br>a = +28.8<br>b = +22.0 |
| 6 | Sodium 1,2-naphthoquinone-4-sulfonate (0.66 g) | 2.8 | 20 g | Bordeaux red | L = 42.8<br>a = +34.3<br>b = −0.0 |
| 7 | 4-Amino-1,2-naphthoquinone hemihydrate (0.87 g) | 7.4 | 19 g | orange | L = 52.7<br>a = +35.8<br>b = +41.8 |
| 8 | 9,10-Phenanthrenequinone (0.55 g) | 7.8 | 20 g | orange-yellow | L = 59.1<br>a = +25.2<br>b = +25.9 |
| 9 | 1,4-Benzoquinone (0.27 g) | 5.9 | — | fox-orange | L = 49.1<br>a = +20.3<br>b = +18.8 |
| 10 | 2-Methyl-1,4-benzoquinone (0.30 g) | 5.9 | — | pink-orange | L = 61.8<br>a = +22.5<br>b = +22.7 |
| 11 | 2,5-Diphenyl-1,4-benzoquinone (0.65 g) | 6.4 | — | yellow | L = 76.1<br>a = +5.1<br>b = +23.3 |
| 12 | 2,5-Dihydroxy-1,4-benzoquinone (0.35 g) | 3.0 | — | reddish mahogany | L = 31.8<br>a = +22.3<br>b = +20.7 |

TABLE 1-continued

| Example No. | Quinone Used | pH | Ethanol Added | Color Shade | Color Values |
|---|---|---|---|---|---|
| 13 | 2,3,5,6-Tetra-hydroxy-1,4-benzo-quinone (0.52 g) | 3.6 | — | orange | L = 34.2<br>a = +27.5<br>b = +30.4 |
| 14 | 2,5-Di[(2-hydroxy-ethyl)amino]-1,4-benzoquinone (0.56 g) | 7.0 | — | yellow | L = 70.7<br>a = +9.7<br>b = +23.9 |
| 15 | 1,4-Naphthatene-dione (0.39 g) | 7.4 | — | brownish mahogany | L = 31.5<br>a = +14.2<br>b = +9.3 |
| 16 | 5,8-Dihydroxy-1,4-naphthalene-dione (0.47 g) | 9.8 | — | brown | L = 35.2<br>a = +10.7<br>b = +5.4 |
| 17 | 1H-Indole-4,7-dione (0.37 g) | 7.0 | — | copper-brown | L = 54.6<br>a = +14.2<br>b = +26.3 |

What is claimed is:

1. An agent (A) for coloring fibers which is prepared before use by mixing two components (A1) and (A2), characterized in that component (A1) contains at least one 2-benzothiazolinone hydrazone derivative of formula (I) or a physiologically tolerated salt thereof

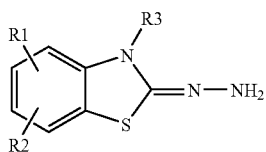

(I)

wherein

R1 and R2 can be equal or different and independently of each other denote hydrogen, a halogen atom, a $(C_1-C_4)$-alkyl group, a halogen-substituted $(C_1-C_4)$-alkyl group, a $(C_1-C_4)$-alkoxy group, a sulfo group, a sulfamoyl group, a carboxyl group, a nitro group, an acetamido group or an $NR^aR^b$ group wherein the $R^a$ and $R^b$ groups can be equal or different and independently of each other denote hydrogen, a $(C_1-C_6)$-alkyl group, a carbocyclic or heterocyclic, substituted or unsubstituted aromatic grouping, or $R^a$ and $R^b$ together with the nitrogen atom form a saturated or unsaturated, substituted or unsubstituted heterocyclic $(C_3-C_6)$ group; or R1 and R2 together with the remainder of the molecule form a heterocyclic or carbocyclic, substituted or unsubstituted ring system;

R3 denotes a $(C_1-C_4)$-alkyl group, a halogen-substituted $(C_1-C_4)$-alkyl group, a sulfo-$(C_1-C_4)$-alkyl group, an acetyl group, a formyl group, a substituted or unsubstituted benzyl group or an isocyclic or heterocyclic grouping;

and component (A2) contains at least one ortho-quinone of formula (II) or para-quinone of formula (III)

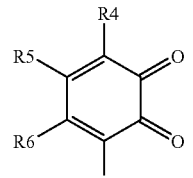

(II)

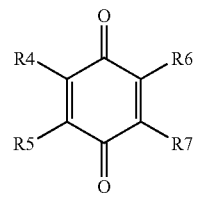

(III)

wherein

R4, R5, R6 and R7 independently of each other denote hydrogen, chlorine, bromine, fluorine, a hydroxyl group, a straight-chain or branched $(C_1-C_6)$-alkyl group, a straight-chain or branched monohydroxy-$(C_1-C_6)$-alkyl group, a straight-chain or branched polyhydroxy-$(C_2-C_6)$-alkyl group, a straight-chain or branched $(C_1-C_6)$-alkoxy group, a straight-chain or branched mono-$(C_1-C_6)$-alkoxy-$(C_1-C_6)$-alkyl group, a straight-chain or branched-poly-$(C_1-C_6)$-alkoxy-$(C_2-C_6)$-alkyl group, a $(C_1-C_2)$-alkylenedioxy group, a sulfo group, a cyano group, a straight-chain or branched amino-$(C_1-C_6)$-alkyl group, an —$NR^aR^b$ amino group wherein the $R^a$ and $R^b$ groups can be equal or different and independently of each other denote hydrogen, a $(C_1-C_6)$-alkyl group, a carbocyclic or heterocyclic, substituted or unsubstituted aromatic grouping, or $R^a$ and $R^b$ together with the nitrogen atom form a saturated or unsaturated, substituted or unsubstituted heterocyclic $(C_3-C_6)$-group;

or in o-quinones of formula (II) R4 and R5 and/or R6 and R7 or R5 and R6, or in p-quinones of formula (III) R4 and R5, and/or R6 and R7 always together with the remainder of the molecule form a heterocyclic or carbocyclic, substituted or unsubstituted ring.

2. The agent according to claim 1, characterized in that the 2-benzothiazolinone hydrazone derivative of formula (I) is selected from among 3-methyl-2-benzothiazolinone hydrazone hydrochloride, 3-ethyl-2-benzothiazolinone hydrazone hydrochloride, 3-phenyl-2-benzothiazolinone hydrazone hydrochloride and 3-benzyl-2-benzothiazolinone hydrazone hydrochloride.

3. The agent according to claim 1, characterized in that the ortho-quinone of formula (II) is selected from among 4,5-dimethoxy-3,5-cyclohexadiene-1,2-dione, 5(5H),6(6H)-diketo-1,3-benzodioxole, 2,3-dihydro-1,4-dimethyl-3-hydroxy-1H-indole-5,6-dione, 2,3-dihydro-3-hydroxy-4-methoxy-1-methyl-1H-indole-5,6-dione, 3,5-di(1,1-dimethylethyl)-3,5-cyclohexadiene-1,2-dione, 2,3-dihydro-3-hydroxy-1-methyl-1H-indole-5,6-dione, 3,4,5,6-tetrachloro-3,5-cyclohexadiene-1,2-dione, 4,5-dimethoxy-3,6-diphenyl-3,5-cyclohexadiene-1,2-dione, 4,5-di(phenylamino)-3,5-cyclohexadiene-1,2-dione, cacotheline, ammonium 3,4-dihydro-3,4-diketo-1-naphthalenesulfonate, 4-methoxy-1,2-naphthalenedione, 1,2-naphthalenedione, sodium 1,2-naphthalenedione-4-sulfonate, 4-amino-1,2-naphthalenedione hydrate (2:1) and 9,10-phenanthrene quinone.

4. The agent according to claim 1, characterized in that the para-quinone of formula (III) is selected from among 1,4- benzoquinone, 2-methyl-1,4-benzoquinone, 2-tert.butyl-1,4-benzoquinone, 2-phenyl-1,4-benzoquinone, 2,5-dimethyl-1,4-benzoquinone, 2,6-dimethyl-1,4-benzoquinone, 2-methyl-5-(1-methylethyl)-1,4-benzoquinone, 2,5-ditert.butyl-1,4-benzoquinone, 2,6-ditert.butyl-1,4-benzoquinone, 2,5-diphenyl-1,4-benzoquinone, 2,3,5,6-tetramethyl-1,4-benzoquinone, 2-methoxy-1,4-benzoquinone, 2-methoxy-5-methyl-1,4-benzoquinone, 2,5-dimethoxy-1,4-benzoquinone, 2,6-dimethoxy-1,4-benzoquinone, 2,3-dimethoxy-5-methyl-1,4-benzoquinone, 2,6-dimethoxy-5-methyl-1,4-benzoquinone, 2,5-dihydroxy-1,4-benzoquinone, 2,5-dihydroxy-3-methyl-1,4-benzoquinone, 2,5-dihydroxy-3-methoxy-6-methyl-1,4-benzoquinone, 2,5-dihydroxy-3,6-diphenyl-1,4-benzoquinone, 3-hydroxy-2-methoxy-5-methyl-1,4-benzoquinone, 2-hydroxymethyl-6-methoxy-1,4-benzoquinone, 2,3,5,6-tetrahydroxy-1,4-benzoquinone, 2-bromo-1,4-benzoquinone, 2-chloro-1,4-benzoquinone, 2-fluoro-1,4-benzoquinone, 2-bromo-5-methyl-1,4-benzoquinone, 2,5-dibromo-1,4-benzoquinone, 2,5-dibromo-3,6-diphenyl-1,4-benzoquinone, 2,5-dibromo-3-methyl-6-(1-methylethyl)-1,4-benzoquinone, 2-chloro-6-methyl-1,4-benzoquinone, 2,5-dichloro-1,4-benzoquinone, 2,6-dichloro-1,4-benzoquinone, 2,5-dichloro-3,6-dimethyl-1,4-benzoquinone, 2,3-dichloro-5,6-cyano-1,4-benzoquinone, 3,6-diketo-1,4-cyclohexadiene-1,2-dicarbonitrile, 2,5-dichloro-3,6-diketo-1,4-cyclohexadiene-1,4-dicarbonitrile, 2,5-dichloro-3,6-dihydroxy-1,4-benzoquinone, 2,5-dichloro-3,6-dimethylamino-1,4-benzoquinone, 2,3,5,6-tetrabromo-1,4-benzoquinone, 2,3,5,6-tetrachloro-1,4-benzoquinone, 2,3,5,6-tetrafluoro-1,4-benzoquinone, 2-amino-5-methyl-1,4-benzoquinone, 5-amino-2-chloro-1,4-benzoquinone, 2,5-di[(2-hydroxyethyl)amino]-1,4-benzoquinone, 2,5-diamino-3,6-dichloro-1,4-benzoquinone, 1,4-naphthalenedione, 5,8-dihydroxy-1,4-naphthalenedione and 1H-indole-4,7-dione.

5. The agent according to claim 1, characterized in that it contains each of the 2-benzothiazolinone hydrazone derivatives of formula (I) and ortho-quinones of formula (II) and/or para-quinones of formula (III) in the dye carrier composition in a total amount from 0.02 to 20 wt. %.

6. The agent according of claim 1, characterized in that it contains additionally from 0.02 to 20 wt. % of a physiologically harmless, direct dye from the group consisting of cationic and anionic dyes, disperse dyes, nitro dyes, azo dyes, quinone dyes and triphenylmethane dyes.

7. The agent according to claim 1, has a pH from 3 to 12.

8. The agent according to claim 1, characterized in that it is a hair colorant.

9. A method for coloring hair comprising applying to the hair a ready-to-use colorant (A) that prepared just before use by mixing components (A1) and (A2) according to claim 1, and optionally with addition of an alkalinizing agent or an acid and then applied the mixture to the hair and after an exposure time of 5 to 60 minutes at a temperature of 20 to 50° C. the hair is rinsed with water, optionally washed with a shampoo and then dried.

10. A multicomponent kit for coloring hair, consisting of component (A1) and component (A2) according to claim 1, and optionally an agent for adjusting the pH.

* * * * *